United States Patent [19]

van Eijl

[11] Patent Number: 4,714,793

[45] Date of Patent: Dec. 22, 1987

[54] PROCESS FOR SEPARATING AN ETHYLENICALLY UNSATURATED HYDROCARBON FROM A HYDROCARBON MIXTURE

[75] Inventor: Ahazuérus T. van Eijl, Terneuzen, Netherlands

[73] Assignee: The Dow Chemical Company, Midland, Mich.

[21] Appl. No.: 859,103

[22] Filed: May 2, 1986

Related U.S. Application Data

[62] Division of Ser. No. 524,176, Aug. 17, 1983, Pat. No. 4,596,655.

[51] Int. Cl.$^4$ .............................................. C07C 7/20
[52] U.S. Cl. ............................................ 585/4; 585/2
[58] Field of Search ......................................... 585/2, 4

[56] References Cited

FOREIGN PATENT DOCUMENTS 916553  1/1963  United Kingdom .................... 585/2

Primary Examiner—Curtis R. Davis

[57] ABSTRACT

An extractive distillation process for selectively separating an ethylenically unsaturated hydrocarbon from a mixture containing hydrocarbon liquids having similar boiling points wherein an amine acts as a selective solvent and polymerization inhibitor. For example, styrene can be separated from a mixture of styrene and o-xylene using aminoethyl piperazine as the solvent for the distillation.

2 Claims, 2 Drawing Figures

PROCESS FOR SEPARATING AN ETHYLENICALLY UNSATURATED HYDROCARBON FROM A HYDROCARBON MIXTURE

CROSS REFERENCE TO RELATED APPLICATION

This is a divisional of application Ser. No. 524,176, filed Aug. 17, 1983, now U.S. Pat. No. 4,596,655.

BACKGROUND OF THE INVENTION

This invention relates to an improved process for the separation of an ethylenically unsaturated hydrocarbon from a hydrocarbon mixture containing same.

Various hydrocarbon mixtures are obtained from the thermal cracking of petroleum products such as naphtha, gas oil, light oil, crude oil, etc. A typical hydrocarbon mixture from cracking operations is pyrolysis gasoline which contains generally aromatic and cycloparaffinic compounds having 5–10 carbon atoms. A typical hydrocarbon mixture obtained following the removal of the hydrocarbons containing 5 carbon items is given in Table A:

TABLE A

| Compound | % by Weight |
| --- | --- |
| Non-aromatics | 16–18 |
| Benzene | 33–37 |
| Toluene | 16–20 |
| Ethylbenzene | 1–2 |
| p/m Xylenes | 5–7 |
| o-Xylene | 2–3 |
| Styrene | 6–8 |
| Dimethylcyclopentadiene | <1 |
| C$_9$ Aromatics | ~1 |
| α-Methylstyrene | <1 |
| Vinyltoluene | 2.5–3 |
| Indene | 2.5–3 |
| Methyl indene | <1 |
| Naphthalene | <1 |
| Phenylacetylene | 0.1 or less |

It should be understood that the above hydrocarbon misture is used to illustratre a typical hydrocarbon mixture and is not presented to define such mixture since such hydrocarbon mixtures may vary greatly.

One of the commercially more valuable components found in the above mixture is styrene. An economical means for separating out this preferred component has been long sought after. The removal of styrene from these mixtures by fractional distillation is rendered unfeasible owing to the presence of other components in the hydrocarbon mixture, especially o-xylene, which have boiling points very close to that of styrene, Table B presents the boiling points of styrene and other hydrocarbons.

TABLE B

| Compound | Boiling Point °C. |
| --- | --- |
| α-Methylstyrene | 163.4 |
| n-Propylbenzene | 159.2 |
| Cumene | 152.4 |
| Cyclooctane | 148.5 |
| Styrene | 145.2 |
| O—Xylene | 144.4 |
| 3-Methyloctane | 143–144 |
| Cyclooctene | 138–143 |
| Phenylacetylene | 142.4 |
| 4-Methyloctane | 141–142 |
| m-Xylene | 139.1 |
| p-Xylene | 138.4 |
| Ethylbenzene | 136.2 |
| Toluene | 110.6 |

One of the more widely used processes for utilizing this styrene involves hydrogenating the styrene to ethylbenzene and thereafter separating it from the xylenes by precision fractional distillation. Following this distillation, the ethylbenzene is then dehydrogenated to styrene and again purified by another distillation. This method is very complicated and expensive. The disadvantages of the aforementioned method have promoted research concerning the direct separation of styrene from the hydrocarbon mixture without first converting the styrene to ethylbenzene.

British Pat. No. 1,038,606 proposes a process utilizing an aqueous solution of a silver salt such as AgNO$_3$ to extract styrene from a hydrocarbon mixture following treatment of the mixture with fuller's earth to prevent slime formation. This method has the disadvantage of being expensive due to the use of silver salts.

Also, U.S. Pat. No. 3,328,267 proposes a process consisting of extractive distillation for the separation of styrene from o-xylene using a di-lower-alkyl formamide such as dimethyl formamide as the extractive distillation solvent. This process also makes use of a polymerization inhibitor such as quinone or hydroquinone or preferably p-tert-butylpyrocatechol. However, the styrene produced by this process has the undesirable characteristic of being light yellow in color. Also, the polymerization inhibitor requires low temperatures to be effective.

U.S. Pat. No. 3,580,839 (Fuerst) entitled, "Recovery of Aromatic Hydrocarbons from Mixtures of Hydrocarbons by Selective Extraction with a Substituted Piperazine Solvent", describes the use of piperazine derivatives having the general formula:

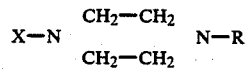

where X denotes formyl or acetyl and R denotes lower alkyl, as extractants for recovering mono- or di-nuclear aromatic hydrocarbons which may have lower (1–4 C) aliphatic hydrocarbon radical substituents from hydrocarbon mixtures. Thus, this process proposes the separation of a hydrocarbon mixture into two fractions; one fraction containing predominantly aromatic hydrocarbons such as benzene, toluene, xylene, ethylbenzene and styrene; and another fraction having a residue predominate in paraffins, olefins or cycloparaffins. The piperazine derivatives may be used in a pure form or mixed with other extractants such as tetramethylsulfone, diethylene glcyol or triethyl glycol. N-formyl-N'-methyl piperazine is the preferred extractant. This process is directed toward a gross separation of products.

In U.S. Pat. No. 3,684,665, Abe et al, proposes a method for separating styrene from hydrocarbon mixtures containing xylenes which comprises extractively distilling a hydrocarbon mixture with a suitable solvent causing the styrene to be concentrated in the solvent from which it can then be removed. Suitable solvents include dialkyl acetamides such as dimethylacetamide, as well as dialkylsulfoxides, alkylene carbonates, lactones, lactums, phenol, alkylphenols, salicyclic acid, alkyl esters, aniline, alkyl anilines, phthalic acid alkyl esters, tetraalkyl ureas, N,N-dialkyl carbamic esters and glycol monoalkyl ethers such as diethylene glycol monoalkyl ether and N-methyl-pyrrolidone. Use of a polymerization inhibitor such as hydroquinone, tert-butylcatechol, phenothiozine, sulfur or mixtures thereof, is urged to prevent polymerization of the styrene. This process, however, suffers from the disadvantages of polymerization losses especially at temperatures above 100° C. and the production of styrene that is undesirably yellow in color.

In U.S. Pat. No. 3,763,015, Morimoto et al, present another extractive distillation process utilizing a polar organic solvent in the presence of a nitrile polymerization inhibitor. Following extractive distillation, the solvent containing styrene is treated with nitric acid and then again distilled to remove impurities and separate the styrene from the solvent. Suitable solvents for this process are given as diethylacetamide, β-methylpropionitrile, butyl lactone, N-methylpyrrolidone, dimethylformamide and dimethylsulfoxide. The preferred polymerization inhibitors are sodium nitrite or potassium nitrite used in combination with a compound having at least one nitro, nitroso, quinoide, phenolic or hydroxy group in the molecule. The preferred additives are p-tert-butyl-catechol, hydroquinone, p-benzoquinone, p-dinitrosobenzene, α-nitro-β-naphthol, o-nitrosonaphthol and α-naphthoquinone. This process produces a yellow styrene product requiring further treatment with nitric acid to remove the colored impurities. Also, yield losses through polymerization are a problem.

In view of the aforementioned deficiencies of the prior processes, it is highly desirable to provide a process for effectively separating a monovinylidene aromatic or other ethylenically unsaturated hydrocarbon from hydrocarbon mixtures containing same while coincidently inhibiting polymerization to produce a substantially pure, color-free product.

SUMMARY OF THE INVENTION

The present invention provides a process for separating an ethylenically unsaturated hydrocarbon from a hydrocarbon mixture characterized by (a) contacting a hydrocarbon mixture containing the unsaturated hydrocarbon with a soluble amine containing more than one amine group and which (1) is sufficiently electronegative to allow a selective separation of the unsaturated hydrocarbon from the hydrocarbon mixtur, (2) inhibits polymerization of the unsaturated hydrocarbon and (3) has a boiling point sufficiently different from the unsaturated hydrocarbon to allow separation of the amine therefrom following a selective separation of the unsaturated hydrocarbon from the hydrocarbon mixture;

(b) separating said amine/hydrocarbon mixture into at least two fractions, one of which contains amine and the unsaturated hydrocarbon.

Subsequently the unsaturated hydrocarbon can be removed from the amine fraction or processed further without said removal.

By soluble amine (hereinafter termed amine) is meant amine soluble in a styrene/hydrocarbon mixture over the range of operating temperatures.

Surprisingly, in an extractive distillation process using an amine as described, an ethylenically unsaturated hydrocarbon can effectively be separated from a hydrocarbon mixture containing same without the addition of other solvents and/or polymerization inhibitors such as those described by U.S. Pat. Nos. 3,763,015 and 3,684,665. Using said process, an unsaturated aliphatic hydrocarbon such as butadiene or acetylene or monovinylidene aromatic such as styrene or vinyltoluene having unexpectedly high purity and/or desirable color can be obtained without significant losses due to polymerization. In a preferred embodiment of the present invention, the amine is N-(aminoethyl)piperazine (AEP). In a particularly preferred embodiment, AEP is employed as the amine solvent or extractant in an extractive distillation process for the separation of styrene from a hydrocarbon mixture containing styrene. Due to the removal of color bodies by the AEP, a styrene having a commercially desirable color can be recovered in purities often exceeding 99 percent.

BRIEF DESCRIPTION OF THE DRAWINGS

Understanding of the present invention is facilitated by reference to the accompanying drawings, in which.

DETAILED DESCRIPTION OF THE INVENTION

The process of the invention is best revealed through a basic discussion of extractive distillation. Extractive distillation refers to processes where a high boiling material, often referred to as an extractive distillation solvent, is added to change the relative volatility of a hydrocarbon mixture to be subsequently separated using extractive distillation techniques. In general, there are two primary reasons for adding such a solvent.

The first reason is to alter the relative volatility of two or more components in the feed stream. Specifically, one or more components may have similar vapor pressures and would distill off together unless the relative volatilities of the components are changed. For example the solvent will change the relative volatilities of an unsaturated compound and also change the relative volatilities of a material having an acetylenic unsaturation as compared to a material having an ethylenic unsaturation.

The second reason for using the solvent is to prevent azeotropic formation of the feed mixture components. The solvent added generally has a boiling point much higher than the components of the feed mixture thereby preventing azeotrope formation.

Figure 1:
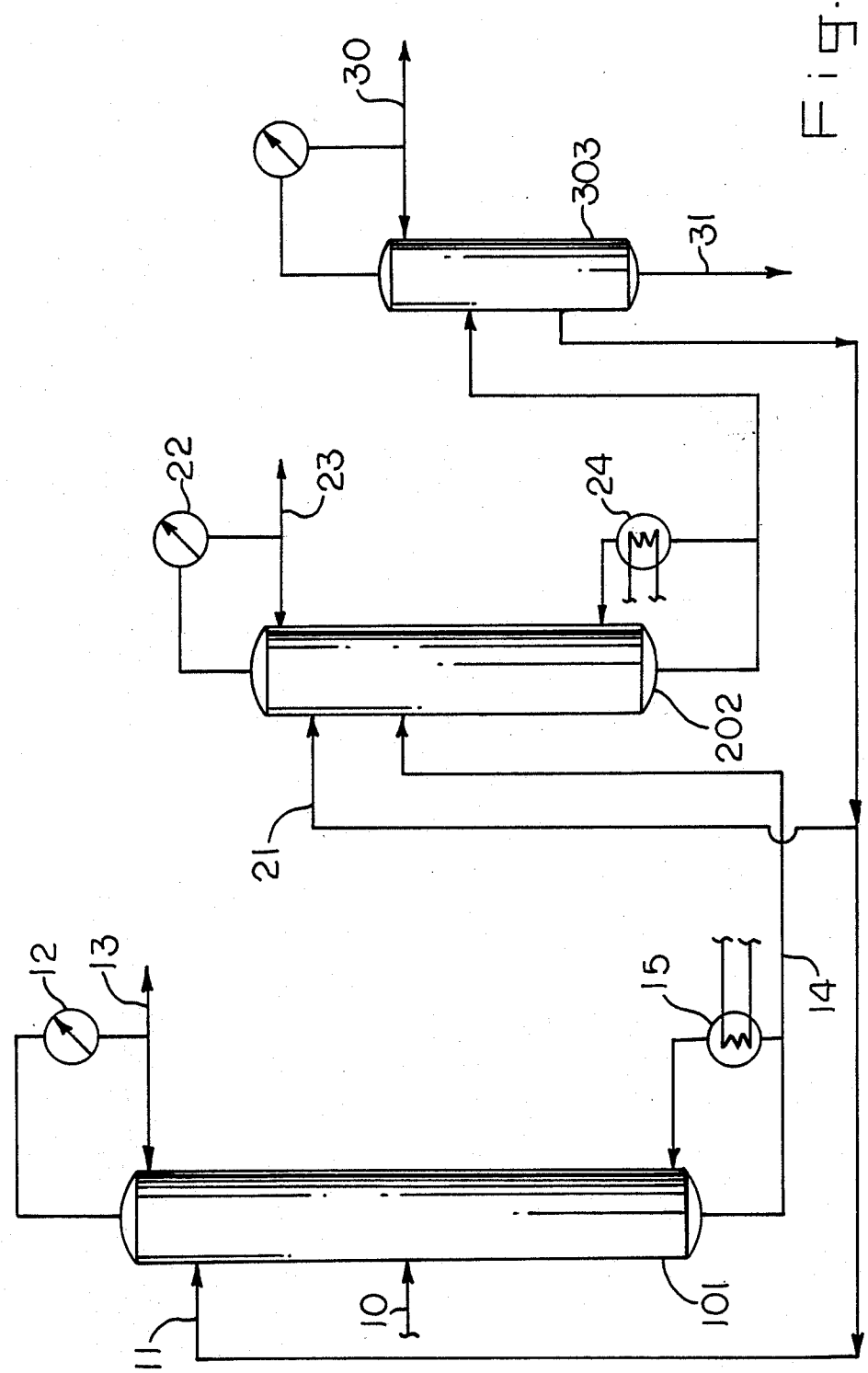
FIG. 1 is a schematic representation depicting an embodiment of the present invention which is particularly usual in the separation of vinyltoluene from a mixture comprising vinyltoluene and other C-9 aromatics, or the separation of acetylene from a mixture containing butadiene and butene.

Referring more particularly to the drawings,

FIG. 1 schematically illustrates an embodiment of the present invention wherein an ethylenically unsaturated hydrocarbon, e.g. vinyltoluene is separated from a hydrocarbon mixture containing same utilizing an extractive distillation column. In the embodiment illustrated, the hydrocarbon mixture containing the unsaturated hydrocarbon is supplied to an extractive distillation column 101 by means of line 10. An amine solvent, preferably N-aminoalkylpiperazine, is aded to the column 101 by means of line 11. Since it is generally desirable to maintain a high concentration of the amine throughout the extraction distillation column and the amine is generally less volatile than the components of the hydrocarbon feed, the amine is preferably added to the column above the point where the hydrocarbon feed enters the column. It is also preferable to add the solvent a sufficient distance below the top of the distillation column to reduce the concentration of the amine in the ascending vapors to a negligible amount before the overhead product is withdrawn. The vapor exiting from the top of column 101 is passed to an overhead condenser 12 which condenses the vapor. A portion of the condensed vapor is returned to the column 101 as liquid overflow. A line 13 carries off the distillate, which distillate, in the separation of vinyltoluene from a hydrocarbon mixture containing vinyltoluene and α-methyl styrene, dicyclopentadiene or 1,2,4- or 1,2,3-trimethyl styrene generally contains the α-methyl styrene and/or dicyclopentadiene. The extractant, i.e., the ethylenically unsaturated hydrocarbon such as the vinyl toluene, and high boiling components (bottoms) of the hydrocarbon feed, are removed from the bottom of the column 101 via a line 14. Owing to the relatively high boiling point of the amine, the bottoms removed by line 14 generally contain a high concentration of the amine. The material removed through line 14 generally is passed through a reboiler 15 which returns a portion of these components as reboil vapor to the column 101.

The portion of the bottoms material not returned to the column 101 enters a stripping column 202. As illustrated in the embodiment shown in FIG. 1, additional amine is introduced into the stripping column 202 via line 21 above the entrance of the bottoms material to the column. Although this further addition of amine is not necessary for the process of the present invention, it is preferred, particularly when the bottoms exiting from column 101 contain phenyl acetylene or high boiling materials other than the amine. The unsaturated hydrocarbon is passed from column 202 as a vapor to a condensor 22 which condenses the gaseous material. A portion of the condensed material is returned to the column 202 and the remainder removed through line 23. The material in line 23 is essentially pure, e.g., at least 98 percent pure, preferably at least 99 percent pure, and of excellent color.

The amine, with any impurities it may contain, exits from the bottom of the stripping column 202, and a portion of this material is passed through a reboiler 24. Since the remaining portion generally contains some high boiling materials and impurities, e.g., polymeric materials or the like, the amine is advantageously purified prior to reuse. Such purification is generally effected by means of a subsequent distillation. In FIG. 1, this purification is performed by introducing the amine into a purification column 303, distilling off the more volatile impurities via line 30 and returning the amine to both the extractive distillation column and the stripping column via line 11. Heavier or less volatile impurities may be removed via line 31.

Figure 2:
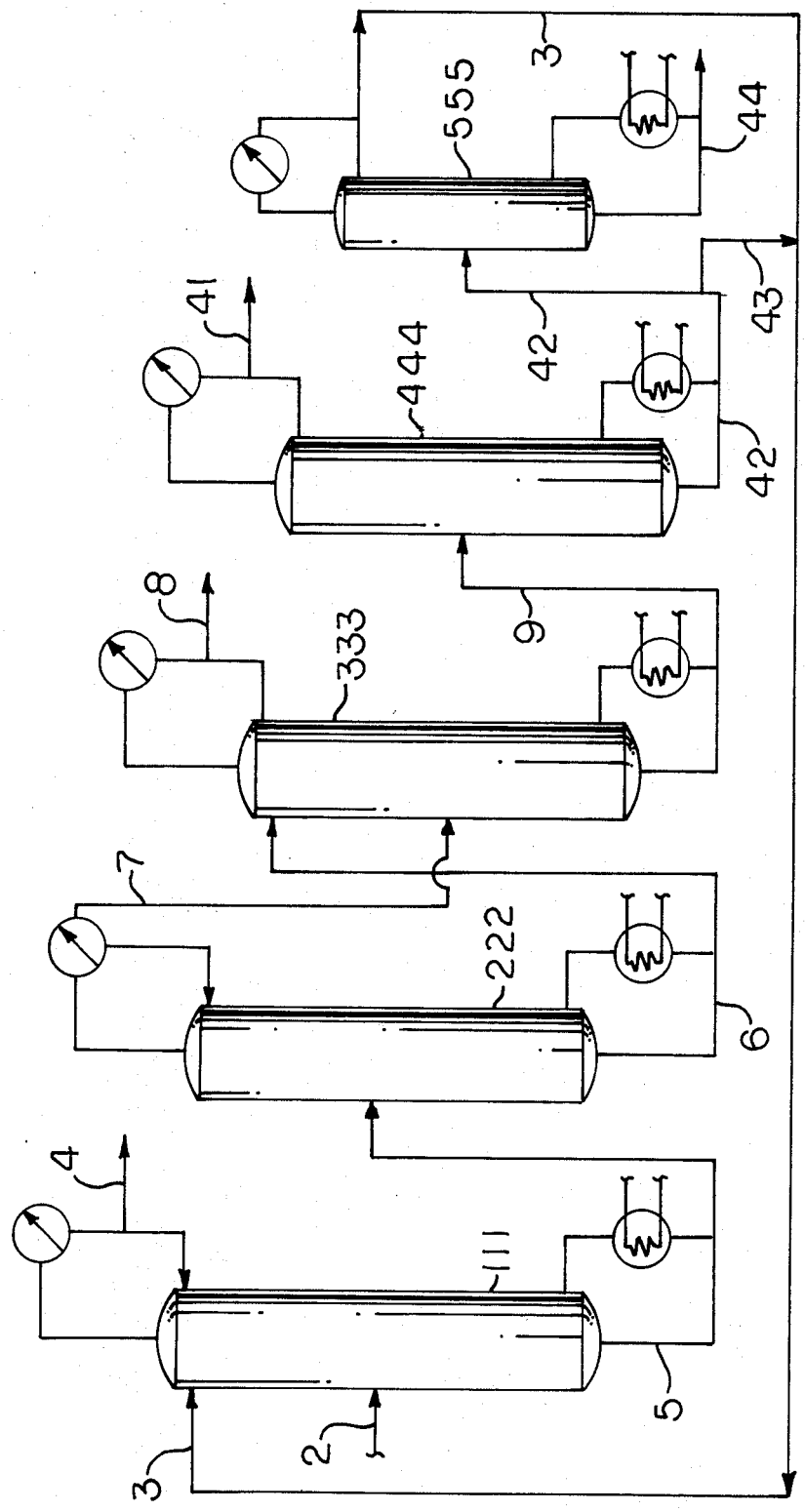
FIG. 2 is a schematic representation depicting an alternative and more preferred embodiment of the present invention which embodiment is particularly useful for separating styrene from a hydrocarbon mixture comprised primarily of hydrocarbon having from 6 to 10 carbon atoms.

FIG. 2 illustrates a preferred embodiment of the present invention particularly useful for the recovery of styrene from the hydrocarbon products obtained in the cracking of petroleum products such as naphtha, gas oil, light or crude oil and the like. The preferred embodiment illustrated in FIG. 2 includes:

(a) a first extractive distillation column 111 for separating styrene from close boiling liquids such as xylenes, particularly o-xylene, and ethylbenzene;

(b) a solvent stripper column 222 for the removal of styrene, high boiling materials such as phenyl acetylene and high boiling impurities from the amine solvent;

(c) a second extractive distillation column 333 for the separation of the high boiling materials and impurities from the styrene;

(d) a solvent recovery column 444 fdr the removal of high boiling materials and impurities such as phenyl acetylene from the amine; and (e) a solvent purification columns 555, for the removal of heavy impurities such as polymers from the amine.

In the recovery of styrene from a hydrocarbon mixture resulting from a cracking operation, a pre-distillation column (not shown) for removing the light hydrocarbons, e.g., hydrocarbons generally having 5 or less carbon atoms, and a predistillation column (not shown) for removing the heavy hydrocarbons, e.g., hydrocarbons generally having 11 or more carbon atoms, are often advantageously employed prior to the introduction of the hydrocarbons to column 111. In such a case, the removal of the light and heavy hydrocarbons is advantageously effected in conditions productive of a hydrocarbon fraction having a boiling point at atmospheric pressure of from 120° to 160° C., preferably from 125° to 155° C.

In such an operation, the hydrocarbon mixture containing styrene is introduced into the first extractive distillation column through line 2. An amine is introduced into this first extractive distillation column 111 at a point above the point where the hydrocarbon mixture is introduced into the column 111. This amine feed is also located a few trays (either actual or theoretical) below the top of the column 111 to reduce the concentration of the amine in the overhead product. The vapor exiting from the top of column 111 is passed to an overhead condenser which condenses the vapor and returns a portion of it to the column. A line 4 carries off a distillate for further processing and/or subsequent use. Generally speaking, the distillate comprises primarily xylene and ethylbenzene. A portion of the material exiting from the bottom of column 111, which generally comprises the separated styrene, amine, phenyl acetylene and higher boiling hydrocarbons and impurities, e.g., polymeric materials, is transferred to the solvent stripping column 222 through line 5. The remaining portion of this material passes through a reboiler which returns the material to column 111.

In solvent stripper 222, the amine is separated from the styrene. The separated amine is passed from the btoom of colum 222 and introduced near the top of the extractive distillation column 333. The separated styrene, which generally contains phenyl acetylene and other impurities, exits from the top of column 222, is condensed and a portion of the condensed material passed to column 333 through line 7 at a point below the introduction of the amine. In this second extractive distillation column 333, the styrene is separated from the phenyl acetylene and high boiling materials, with a relatively pure, preferably at least 99 percent pure, styrene exiting from the top of column 333. The relatively pure material is condensed and removed through line 8 for subsequent use. The amine containing the phenyl acetylene and/or high boiling materials exits from column 333 and a portion thereof is transferred to the solvent recovery column 444 through line 9. In the solvent recovery column 444, the amine and phenyl acetylene, are separated. The phenyl acetylene exits from the top of column 444, is condensed and a portion thereof removed by means of line 41 for subsequent use. The amine which now contains the higher boiling impurities, e.g., the polymeric materials, is removed from column 444 by means of line 42. A portion of this material is passed through a reboiler and returned to the column 444. A second and, generally, relatively large proportion of the material is returned by means of line 43 to line 3 for reuse in the first extractive distillation column 111. The remainder of the amine and the impurities having the higher boiling points are introduced into a solvent purification column 555 by means of line 42. In column 555, the amine is separated from the high boiling impurities. The separated amine, which is now relatively pure, exits from the top of column 555 and is returned to line 3 for subsequent reuse in column 111. The heavy impurities ar removed from the bottom of column 555 by means of line 44.

It will be apparent to those skilled in the art that certain process features might be modified, deleted or added according to the particular process parameters chosen and that such choice depends upon many diverse practical considerations such as economy, convenience and energy conservation.

For example, while a high concentration of the ethylenically unsaturated hydrocarbon being separated in the hydrocarbon feed is preferred, lower concentrations are suitable and fall within the scope of the invention. However, a predistillation may be advantageously carried out in order to obtain a hydrocarbon feed having a higher concentration of the unsaturated hydrocarbon and thereby improve the overall efficiency of the separation process. Moreover, components which exhibit similar volatility to the amine may decrease the performance of the amine and preferably should be removed. It should be clear from the above discussion that a plurality of separation columns utilized at different points in the overall process such as introduction of the hydrocarbon feed, amine recovery, etc. and/or techniques may be used for removal and/or purification of the various streams. Also the extractive distillation part of the process in which use is made of an amine as solvent may take place in one or more columns with the possibility of the amine solvent recovery operation interspersed between said columns.

With regard to the materials employed in the practice of the present invention, the hydrocarbon mixture from which the ethylenically unsaturated hydrocarbon is separated is a mixture comprising two or more hydrocarbons at least one of which is the ethylenically unsaturated hydrocarbon to be subsequently separated. The ethylenically unsaturated hydrocarbon is a hydrocarbon having an ethylenic unsaturation between two carbon atoms, which atoms are not part of an aromatic ring, including the alkadienses such as butadiene, the acetylenes and the monovinylidene aromatics such as styrene, alkyl-substituted styrenes such as vinyltoluene and ethylvinylbenzene and vinylnaphthalene. The other hydrocarbon component(s) may contain an ethylenic unsaturation, e.g., vinyltoluene is often present in the separation of styrene from a thermally cracked petroleum product, but, in general, the other components are predominantly hydrocarbons having no ethylenic unsaturation and include saturated aliphatics and cycloaliphatics, and aromatics. In addition, the hydrocarbon mixture may optionally contain one ore more inorganic components or substituted hydrocarbon components. The process of the present invention is particularly useful for the separation of monovinylidene aromatic, in particular styrene or vinyltoluene, from a hydrocarbon mixture containing one or more aromatic components in addition to the styrene and/or vinyltoluene. Such other aromatic component(s) generally included benzene, toluene ethylbenzene, o-, p- and m-xylene and/or indene. More particularly, the process of the present invention is preferably employed in the separation of styrene from pyrolysis gas and the separation of vinyltoluene from a mixture of vinyltoluene and α-methyl styrene, dicyclopentadiene or 1,2,4- or 1,2,3-trimethylbenzene.

The amine employed in the practice of the present invention is a soluble amine containing more than one amine group and which is 1) sufficiently electronegative relative to the ethylenically unsaturated hydrocarbon to allow the selective separation of the unsaturated hydrocarbon from the hydrocarbon mixture, (2) inhibits the polymerization of the ethylenically unsaturated hydrocarbon and (3) has a boiling point sufficiently high to allow separation of the amine from the unsaturated hydrocarbon following the selective separation of the unsaturated hydrocarbon from the hydrocarbon mixture. By the term "soluble" is meant that the amine forms a solution with the hydrocarbon mixture (i.e., the combination of the amine and hydrocarbon mixtures appears as a uniformly dispersed or homogeneous liquid under visual inspection at no magnification). Generally speaking, the boiling point of the amine is sufficiently high if it exceeds the boiling point of the unsaturated hydrocarbon to be separated by at least 20°, more preferably 30° C., at the pressures employed in the process. Of course, the greater the differences in boiling points, the easier is the subsequent separation.

Amines which are sufficiently electronegative for the purposes of the present invention are those amines which sufficiently change the relative volatility of the unsaturated hydrocarbon being separated with respect to the other compnents in the mixture, particularly the components having boiling points close to that of the unsaturated hydrocarbon (generally by reducing the relative volatility of the unsaturated hydrocarbon) to allow the selective separation of the unsaturated hydrocarbon from the hydrocarbon mixture.

In addition to changing the volatility of the unsaturated hydrocarbon, the amine inhibits the polymerization of the unsaturated hydrocarbon so that less of the unsaturated hydrocarbon is polymerized during its separation in the presence of the amine than if the same hydrocarbon were subjected to an identical treatment except no amine employed. Advantageously, less than 1, preferably less than 0.5, weight percent of the unsaturated hydrocarbon is polymerized during its separation by the method of the present invention.

In general, the amines useful in the process of the present invention contain at least two amino or substituted amino groups, with one amino group preferably being unsubstituted, which amino or substituted amino groups are separated by two or more, preferably two carbon atoms. Representative amines are diethylene triamine and N-aminoalkyl piperazine. While the amines most advantageously employed will vary depending on the hydrocarbon to be separated, the amines which, in general, are preferably employed herein are N-aminoalkyl piperazines having an alkyl group of from 1 to 4 carbon atoms. The most preferred amine is N-aminoethyl piperazine.

The conditions under which the separation of the unsaturated hydrocarbon is most advantageously conducted will vary depending on many factors including the specific amine employed and the composition of the hydrocarbon mixture and the unsaturated hydrocarbon to be separated therefrom. As a specific example, in the preferred embodiment wherein styrene is separated from a hydrocarbon mixture containing o-xylene using an extractive distillation column, the extractive distillation column or columns advantageously have from 90 to 130 theoretical stages, and preferably from 115 to 125 theoretical stages. The stages are advantageously effectuated in packed columns utilizing a packing such as a regular sheet packing or dumped packing. The extractive distillation step is conducted under a combination of pressure and temperature conditions sufficient to effect a separation yet not promote undesirable polymerization. Generally, this means that the bottom temperatures from 120° C. to 140° C. are advanageously empolyed with temperatures from 120° C. to 135° C. being preferred.

Higher temperatures often promote undesirable reactions and lower economic efficiency of the process. To save energy costs and help reduce undesirable reactions, the process is generally operated at reduced pressure. Advantageously, bottom pressures are maintained at from 70 to 125 mm Hg, with a range from 110 to 120 mm Hg being preferred. The same considerations of efficiency and minimizing undesirable reactions apply here. Temperatures at the top of the column advantageously range from 45° C. to 70° C., preferably from 45° C. to 55° C. Advantageously, pressures at the top range from about 30 to 45 mm Hg, with 35 to 45 mm Hg being preferred. The amine/styrene ratio of the hydrocarbon feed with advantageously range from about 5 to about 9, with a ratio of about 8 being preferred.

In another preferred embodiment of the invention wherein styrene is separated from phenyl acetylene by extractive distillation, the extractive distillation column or columns advantageously have from 70 to 80 theoretical stages, with 70 to 75 stages being preferred. The column(s) used in the separation contain trays, typically of the bubble cap type, sieve type or valve type. The stages may also be effectuated by packed column utilizing a packing such as a sheet or dumped packing. Again, the extractive distillation step is conducted under a combination of pressure and temperature conditions sufficient to effect a separation yet not promote undesirable polymerization. Generally speaking, this means that bottom temperatures from 140° C. to 160° C. are advantageously employed with temperatures from 145° C. to 150° C. being preferred. Higher temperatures often promote undesirable reactions and lower temperatures result in lower economic efficiency of the process. The process is generally operated at reduced pressure to save energy costs and to prevent undesirable reactions. Advantageously, bottom pressures from 100 to 120 mm Hg are employed with pressures of about 100 mm Hg preferred. The same considerations of efficiency and minimizing undesirable reactions apply here. Temperatures at the top of the column advantageously range from 45° C. to 70° C., preferably from 45° C. to 55° C. Pressures at the top advantageously range from 30 to 45 mm Hg, with pressures from 35 to 40 mm Hg being preferred. The amine/styrene ratio in the hydrocarbon feed will advantageously vary from 7 to 9, and is preferably about 8.

EXAMPLE 1

The total mixture obtained by the thermal cracking of a petroleum fraction such as naphtha is separated in one of the usual ways, e.g., by distillation either at atmospheric or reduced pressure and a fraction boiling between about 125° C. and 155° C. is obtained. This fraction contains styrene, xylenes, ethylbenzene, paraffins, naphthalene, polyalkyl-substituted aromatics, phenylakynes and dienes having from 4–9 carbon atoms and typically has a APHA color of 65. A typical example of such a mixture is:

| Component | % by weight |
|---|---|
| light hydrocarbons | 0.6 |
| benzene and toluene | 6.0 |
| ethylbenzene | 8.0 |
| m- and p-xylene | 32.2 |
| o-xylene | 14.0 |
| styrene | 37.8 |
| C-9's | 0.7 |
| C-8's and other aromatics | 0.7 |

This mixture is fed to a packed column about 50 meters high and having from about 100 to about 125 theoretical plates, ahd is introduced at about 20 meters below the top of the tower. AEP is fed to the same column at a point situated near the top, e.g., about 2 meters below the top, in a weight ratio of AEP to hydrocarbon feed of about 3:1. The reflux ratio is about 7.5. The top pressure and temperature are about 40 mm Hg and about 60° C., the reboiler temperature is about 130° C. Even with this high temperature the loss due to polymerization is less than 0.2 percent relative to the styrene present in the feed. The top product of this column contains only about 1.0 percent styrene and the bottoms product contains almost all the styrene originally present in the feed. The bottoms product containing styrene, AEP and phenyl acetylene is passed to a stripping column where the AEP is recovered substantially free of styrene, phenyl acetylene and any colored bodies. The styrene/phenyl acetylene containing hydrocarbon mixture is passed from the top of this column to a second packed distilling column about 30 meters high and having about 70 to 80 theoretical plates and is introduced about 30 meters below the top of the second distilling column. The AEP recovered from the bottom of the stripping column acts as a solvent and is fed into the second distillation column about 2.5 meters below the top, in a weight ratio of AEP to hydrocarbon feed of about 8:1. The reflux ratio is about 4. The top pressure and temperature are about 35 mm Hg and about 50° C., respectively, and the reboiler temperature is about 55° C.

The top product of this second packed distillation column contains styrene of about 99.6 percent purity and is colorless. Since the AEP acts as a very efficient inhibitor, polymerization of styrene is practically nil in this second distillation column. Any colored compounds present stay in the AEP, so that a high-purity, low-color styrene is obtained from the top of the second column. The APHA color is less than 5 for the styrene product from the second extractive distillation column. Note that the higher the reflux ratio in the extractive distillation column, the greater the dilution of the extractant by increasing the amount of non-extractant material in the liquid overflow with the effect of this dilution generally being a decrease in relative volatilities. The optimum reflux ratio is readily determined for a particular process set up by a skilled operator.

EXAMPLE 2

The procedure of Example 1 is repeated, but now using as the amine diethylene triamine. Here again, a styrene-rich fraction was obtained.

EXAMPLE 3

Using generally the extractive distillation method embodied in FIG. 1 and generally the techniques employed in Example 1 for separating styrene, vinyltoluene is removed from a hydrocarbon mixture containing primarily aromatic hydrocarbons having 9 carbon atoms including α-methylstyrene, 1,2,4-trimethylbenzene and 1,2,3-trimethylbenzene in the presence of N-aminoethyl piperazine. The top product from the extractive distillation column contains less than about 2 percent vinyltoluene whereas the bottom product contains vinyltoluene, indene and aminoethyl piperazine. The vinyltoluene, which possesses excellent color, is easily separated from the indene and/or aminoethyl piperazine using additional extractive distillation columns.

EXAMPLE 4

A hydrocarbon stream containing primarily hydrocarbons having 4 carbon atoms including acetylene, butadiene, butene, isobutene and butane is feed to an extractive distillation column and subsequently distilled in the presence of N-aminoethyl piperazine. The material exiting from the top of the extractive distillation column contains the majority of the butadiene, butene, isobutene and butane contained in the hydrocarbon feed. The bottoms from the columns consist essentially of AEP and acetylenes with only minor amounts of the other C4 hydrocarbons being present.

EXAMPLE 5

A hydrocarbon stream of the following composition:

| Component | % by weight |
|---|---|
| C4 hydrocarbons | 2.2 |
| isopentane | 12 |
| 1-pentene | 4 |
| isoprene | 18 |
| n-pentane | 23 |
| methyl substituted butenes | 8.4 |
| other pentenes | 3.2 |
| cyclopentadiene | 5.6 |
| pentadienes | 10.5 |
| other C5 hydrocarbons | 4.6 |

-continued

| Component | % by weight |
|---|---|
| other hydrocarbons | 8.5 | is fed to a packed distillation column to separate the stream into a top product containing the lighter components (e.g., C4 hydrocarbons) and a bottoms product comprising the remaining components of the hydrocarbon stream. The separated hydrocarbon stream containing the heavier components is fed to a second distillation column to separate the stream into a bottoms product containing the polybutadienes and other heavier components and a top product containing, among other components, the isopentane, n-pentane and isoprene. The top product from this column is admixed with N-(aminoethyl) piperazine (AEP) in a weight ratio of 3 parts AEP for each part of the top product and the resulting admixture is fed to a third distillation column. The relative volatilities of the hydrocarbon components in the stream are now rendered sufficiently different from isoprene such that isoprene having a purity higher than 98 percent can be obtained. One method for obtaining the isoprene is by removing, from the side of the column, the pure isoprene fraction. In another method, no side stream is employed and the bottoms product contains a mixture of isoprene, AEP and cyclopentadiene. In this method, the isoprene is easily separated from the AEP and/or cyclopentadiene using additional extractive distillation columns.

Alternatively, if no AEP is employed, isoprene can only be recovered as a mixture with not insubstantial amounts of isopentane, n-pentane, cyclopentadiene and various other components.

By repeating the described process using a variety of weight ratios of AEP to the isoprene containing hydrocarbon stream, isoprene of differing purities can be obtained. Specifically, as the relative concentration of AEP to the isoprene containing hydrocarbon stream is reduced, the isoprene recovered will generally contain greater amounts of the other components.

The above description and example serve to illustrate the invention and its advantages and should not be interpreted as limiting since further modifications of the disclosed invention will be apparent to those skilled in the art. All such modifications are deemed to be within the scope of the invention as defined by the following claims.

What is claimed is:

1. A process for inhibiting polymerization of styrene characterized by contacting a styrene containing fluid with an N-aminoalkyl piperazine.

2. The process of claim 1 wherein the N-(aminoalkyl)piperazine is N-(aminoethyl)piperazine.

* * * * *